US007709256B2

(12) United States Patent
Warren et al.

(10) Patent No.: US 7,709,256 B2
(45) Date of Patent: *May 4, 2010

(54) DISEASE MODEL INCORPORATION INTO AN ARTIFICIAL IMMUNE SYSTEM (AIS)

(75) Inventors: William L. Warren, Orlando, FL (US); Russell Higbee, Orlando, FL (US); Eric Mishkin, Winter Springs, FL (US); Guzman Sanchez-Schmitz, Orlando, FL (US); Heather Fahlenkamp, Broken Arrow, OK (US); Michael Rivard, Natick, MA (US)

(73) Assignee: Vaxdesign Corp., Orlando, FL (US)

( * ) Notice: Subject to any disclaimer, the term of this patent is extended or adjusted under 35 U.S.C. 154(b) by 39 days.

This patent is subject to a terminal disclaimer.

(21) Appl. No.: 11/453,003

(22) Filed: Jun. 15, 2006

(65) Prior Publication Data

US 2007/0026392 A1 Feb. 1, 2007

Related U.S. Application Data (63) Continuation of application No. 11/116,234, filed on Apr. 28, 2005.

(60) Provisional application No. 60/565,846, filed on Apr. 28, 2004, provisional application No. 60/643,175, filed on Jan. 13, 2005.

(51) Int. Cl.
C12N 5/06 (2006.01)
(52) U.S. Cl. .................................. 435/372; 435/373
(58) Field of Classification Search ............... None
See application file for complete search history.

(56) References Cited

U.S. PATENT DOCUMENTS

| 5,008,116 A | 4/1991 | Cahn |
| 5,160,490 A | 11/1992 | Naughton et al. |
| 5,354,686 A | 10/1994 | Haberman |
| 5,562,910 A | 10/1996 | Daynes et al. |
| 5,725,856 A | 3/1998 | Hudziak et al. |
| 5,739,001 A | 4/1998 | Brown et al. |
| 5,750,329 A | 5/1998 | Quinn et al. |
| 6,177,282 B1 | 1/2001 | McIntyre |
| 6,274,378 B1 | 8/2001 | Steinman et al. |
| 6,479,064 B1 | 11/2002 | Atala |
| 6,835,550 B1 | 12/2004 | Estell et al. |
| 2002/0155108 A1 | 10/2002 | Barbera-Guillem |
| 2003/0109042 A1 | 6/2003 | Wu et al. |
| 2003/0147923 A1 | 8/2003 | Klaviniskis et al. |
| 2003/0199006 A1 | 10/2003 | Britz et al. |
| 2003/0207287 A1 | 11/2003 | Short |
| 2004/0009943 A1 | 1/2004 | Semple et al. |
| 2004/0109876 A1 | 6/2004 | Yamamoto et al. |
| 2004/0234510 A1* | 11/2004 | Mochitate ................. 424/93.7 |
| 2005/0191743 A1* | 9/2005 | Wu et al. ................... 435/366 |
| 2005/0229264 A1 | 10/2005 | Chang et al. |
| 2005/0282148 A1* | 12/2005 | Warren et al. ................. 435/4 |
| 2006/0105454 A1 | 5/2006 | Son et al. ................... 435/325 |
| 2006/0270029 A1* | 11/2006 | Warren et al. ............... 435/325 |
| 2006/0275270 A1* | 12/2006 | Warren et al. ............... 424/93.7 |
| 2007/0015136 A1* | 1/2007 | Sanchez-Schmitz et al. ... 435/4 |
| 2007/0141552 A1* | 6/2007 | Warren et al. ................. 435/4 |
| 2007/0154956 A1* | 7/2007 | Warren et al. ................ 435/7.2 |
| 2007/0178076 A1* | 8/2007 | Drake et al. ............. 424/93.21 |
| 2007/0218054 A1* | 9/2007 | Sukumar et al. ......... 424/133.1 |
| 2008/0008653 A1 | 1/2008 | Tew et al. |

FOREIGN PATENT DOCUMENTS

| EP | 0 358 506 | 9/1989 |
| EP | 1 437 147 | 9/2002 |
| EP | 1970444 A1 | 12/2006 |
| WO | WO 99/15629 | 4/1999 |
| WO | WO 99/43788 * | 9/1999 |
| WO | WO99/49319 | 9/1999 |
| WO | WO 03/041568 * | 5/2003 |
| WO | WO 03/050271 | 6/2003 |
| WO | WO 2004/031361 | 4/2004 |
| WO | WO2004/101773 | 11/2004 |
| WO | WO 2005/104755 | 11/2005 |
| WO | WO 2007/075979 | 7/2007 |
| WO | WO 2007/106559 | 9/2007 |
| WO | WO 2007/146267 | 12/2007 |

OTHER PUBLICATIONS

Dorland Medical Dictionary, 2007 p. 1.*
Stendma's Medical Dictionary, 2007, p. 1.*
Birkness et al Infection and Immunity, 1995, p. 402-409.*
John G. Tew et al., "*Follicular Dendritic Cells and Presentation of Antigen and Costimulatory Signals to B Cells*," Immunological Reviews (1997), vol. 156, pp. 39-52.

(Continued)

*Primary Examiner*—Michail A Belyavskyi
(74) *Attorney, Agent, or Firm*—Roylance, Abrams, Berdo & Goodman LLP (57) ABSTRACT The present invention relates to methods for preparing an artificial immune system. The artificial immune system comprises a cell culture comprising a three-dimensional matrix comprising lymphoid tissue, a three-dimensional matrix comprising epithelial and/or endothelial cells, and diseased cells. The artificial immune system of the present invention can be used for in vitro testing of vaccines, adjuvants, immunotherapy candidates, cosmetics, drugs, biologics and other chemicals.

11 Claims, 4 Drawing Sheets

OTHER PUBLICATIONS

Akiko Furuyama et al., "*Assembly of Basement Membrane in vitro by Cooperation Between Alveolar Epithelial Cells and Pulmonary Fibroblasts*," Cell Structure and Function (1997), vol. 22, pp. 603-614.

Stephen F. Badylak et al., "*Small Intestinal Submucosa: A Substrate for in vitro Cell Growth*," J. Biomater. Sci. Polymer Edn. (1998), vol. 9, No. 8, pp. 863-878.

Shaoli Zhang et al., "*Growth Factors Secreted by Bronchial Epithelial Cells Control Myofibroblast Proliferation: An in vitro Co-culture Model of Airway Remodeling in Asthma*," Laboratory Investigation (1999), vol. 79, No. 4, pp. 395-405.

H. Garrett Thompson et al., "*A Three-dimensional in vitro Model of Angiogenesis in the Airway Mucosa*," Pulmonary Pharmacology & Therapeutics (2007), vol. 20, pp. 141-148.

M. Nakamura et al., "*Expression of Leptin in Two-layered Culture of Gastric Mucous Cells and Fibroblasts: Effect of Helicobacter pylori Attachment*," Aliment Pharmacol Ther. (2004), vol. 20, suppl. 1, pp. 125-130.

Martin N. Nakatsu et al., "*Angiogenic Sprouting and Capillary Lumen Formation Modeled by Human Umbilical Vein Endothelial Cells (HUVEC) in Fibrin Gels: The Role of Fibroblasts and Angiopoietin-1*," Microvascular Research (2003), vol. 66, pp. 102-112.

Per Brandtzaeg et al., "*Mucosal B Cells: Phenotypic Characteristics, Transcriptional, Regulation, and Homing Properties*," Immunological Reviews (2005), vol. 206, pp. 32-63.

Tarte et al., Leukemia, vol. 14, 2000, abstract p. 2182.

Kim et al., "*Three-Dimensional Tissue Culture Models In Cancer Biology*," Seminars in Cancer Biology, (2005), 15(5), pp. 365-377.

A. R. Neves, et al., "*Dendritic Cells Derived From Metastatic Cancer Vaccinated With Allogeneic Dendritic Cell-Autologous Tumor Cell Hybrids Express More CD86 and Induce Higher Levels Of Interferon-Gamma In Mixed Lymphocyte Reactions*," Cancer Immunology and Immunotherapy, (2005), 54(1), pp. 61-66.

S. Büchele et al., "*Presentation of Tetanus Toxoid To Autologous T Cells By Dendritic Cells Generated From Human Blood. Improved Specificity With Dendritic Cells Generated Without Fetal Calf Serum*," Advances in Experimental Medicine and Biology, (1997), vol. 417, pp. 233-237.

Bai et al., "*Generation Of Dendritic Cells From Human Bone Marrow Mononuclear Cells: Advantages From Clinical Applications In Comparison To Peripheral Blood Monocyte Derived Cells*," International Journal of Oncology, (2002), 20(2), pp. 247-253.

K. V. Bromelow et al., "*Whole Blood Assay For Assessment Of The Mixed Lymphocyte Reaction*," Journal of Immunological Methods, (2001), 247(1-2), pp. 1-8.

M. H. Kosco et al., "*Follicular Dendritic Cells and Germinal Center Formation In-Vitro*," Accessory Cells in HIV and Other Retroviral Infections: Morphological and Functional Aspects; Workshop on Morphological and Functional Aspects of Accessory Cells in Tretroviral Infections, Hamberg, Germany, 23-24, p. 44-49 (1991).

M. H. Kosco et al., "*Folicular Dendritic Cell-Dependent B-Cell Proliferation And In Vitro Germinal Center*," Lymphatic Tissues In Vivo Immune Responses, (1991), pp. 687-690.

O. Soderberg et al., "*The Human Follicular Dendritic Cell Line FDC-1 Binds Immune Complexes And Promotes Somatic Hypermutation*," Blood, (2001), 98(11 part 2), pp. 40b.

R. Tsunoda et al., "*Human Follicular Dendritic Cells In Vitro And Follicular Dendritic-Cell-Like Cells*," Cell and Tissue Research, (1997), 288(2), pp. 381-389.

R. Tsunoda et al., "*Follicular Dendritic Cells In Vitro Modulate The Expression Of Fas and Bcl-2 on Germinal Center B Cells*," Cell and Tissue Research, (2000), 299(3), pp. 395-402.

J. G. Tew et al., "*Follicular Dendritic Cells As Accessory Cells*," Immunological Reviews, (1990), No. 117, pp. 185-211.

M. H. Kosco et al., "*Follicular Dendritic Cell-Dependent Adhesion and Proliferation Of B Cells In Vitro*," Journal of Immunology, (1992), 148(8), pp. 2331-2339.

Y. Wu et al., "*Influence Of Follicular Dendritic Cells And Primed T Cells On Somatic Hypermutation In In Vitro Germinal Centers*," Journal of Immunology, (2006), 176(suppl. S), pp. S235-S236.

M. El Shikh et al., "*Follicular Dendritic Cells Stimulated By Collagen Type I Develop Dendrites And Networks In Vitro*," Cell and Tissue Research, (2007), 329(1), pp. 81-89.

R. Seguin et al., "*Human Brain Endothelial Cells Supply Support For Monocyte Immunoregulartory Functions*," Journal of Neuroimmunology, (2003), 135(1-2), pp. 96-106.

S Levenberg et al., "*Advances In Tissue Engineering*," Current Topics In Developmental Biology, (2004), vol. 61, pp. 113-134.

P. Manna et al., "Differentiation And Functional Maturation Of Human CD14<+> Adherent Peripheral Blood Monocytes By Xenogeneic Endothelial Cells: Up-Regulation Of Costimulation Cytokine Generation, And Toll-Like Receptors," Transplantation, (2002), 74(2), pp. 243-252.

International Search Report for PCT/US05/14444, dated Mar. 21, 2008.

International Search Report for PCT/US06/43563, dated Nov. 29, 2007.

International Search Report for PCT/US06/43712, dated Aug. 8, 2007.

International Search Report for PCT/US07/006532, dated Feb. 18, 2008.

International Search Report for PCT/US07/006571, dated Sep. 21, 2007.

Partial International Search for PCT/US07/013745, dated Jan. 28, 2008.

International Search Report for PCT/US07/013871, dated Mar. 3, 2008.

International Search Report for PCT/US06/049128, dated Jun. 12, 2007.

Suematsu, et al., "Generation of a Synthetic Lymphoid Tissue-Like Organoid in Mice," Nature Biotechnology, vol. 22, No. 12, pp. 1539-1545 (Dec. 2004).

Randolph, et al., "Role of Tissue Factor in Adhesion of Mononuclear Phagocytes To and Trafficking Through Endothelium In Vitro," Blood, vol. 92, pp. 4167-4177 (1998).

Randolph, et al., "Differentiation of Monocytes into Dendritic Cells in a Model of Transendothelial Trafficking," Science, vol. 282, pp. 480-483 (1998).

Randolph, et al., "A Physiologic Function for p-Glycoprotein (MDR-1) During the Migration of Dendritic Cells from Skin Via Afferent Lymphatic Vessels," Proc. Natl. Acad. Sci., vol. 95, pp. 6924-2929 (1998).

Randolph, et al., "The CD16(+) (FcγRIII(+)) Subset of Human Monocytes Preferentially Becomes Migratory Dendritic Cells in a Model Tissue Setting," J. Exp. Med., vol. 196, No. 4, pp. 517-527 (2002).

Randolph, et al., "Mononuclear Phagocytes Egress from an In Vitro Model of the Vascular Wall by Migrating Across Endothelium in the Basal to Apical Direction: Role of Intercellular Adhesion Molecule 1 and the CD11/CD18 Integrins," J. Exp. Med., vol. 183, pp. 451-462 (1996).

Randolph, et al., "A Soluble Gradient of Endogenous Monocyte Chemoattractant Protein-1 Promotes the Transendothelial Migration of Monocytes In Vitro," The Journal of Immunology, vol. 155, pp. 3610-3618 (1995).

Furie, et al., "Migration of Neutrophils Across Endothelial Monolayers is Stimulated by Treatment of the Monolayers with Interleukin-1 or Tumor Necrosis Factor-Alpha," The Journal of Immunology, vol. 143, pp. 3309-3317 (1989).

Robbiani, et al., "The Leukotriene C4 Transporter MRPI Regulates CCL19 (MIP-3β, ELC)-Dependent Mobilization of Dendritic Cells to Lymph Nodes," Cell, vol. 103, pp. 757-768 (2000).

Podgrabinska, et al., "Molecular Characterization of Lymphatic Endothelial Cells," Proc. Natl. Acad. Sci. U.S.A., vol. 99, No. 25, pp. 16069-16074 (2002).

Berman, et al., "Roles of Platelet/Endothelial Cell Adhesion Molecule-1 (PECAM-1, CD31) in Natural Killer Cell Transendothelial Migration and Beta 2 Integrin Activation," The Journal of Immunology, vol. 156, pp. 1515-1524 (1996).

Gergel, et al., "Activation of Endothelium by *Borrelia burgdorferi* In Vitro Enhances Transmigration of Specific Subsets of T Lymphocytes," Infection and Immunity, vol. 69, pp. 2190-2197 (2001).

Qu, et al., "Autocrine Type I IFN and Contact with Endothelium Promote the Presentation of Influenza A Virus by Monocyte-Derived APC," The Journal of Immunology, vol. 170, pp. 1010-1018 (2003).

Mellman, et al., "Dendritic Cells: Specialized and Regulated Antigen Processing Machines," Cell, vol. 106, pp. 255-258 (2001).

Lukas, et al., "Human Cutaneous Dendritic Cells Migrate Through Dermal Lymphatic Vessels in a Skin Organ Culture Model," The Journal of Investigative Dermatology, vol. 106, pp. 1293-1299 (1996).

Fransson, et al., "Culture of Human Epidermal Langerhans Cells in a Skin Equivalent," British Journal of Dermatology, vol. 139, pp. 598-604 (1998).

Banchereau, et al., "Immunobiology of Dendritic Cells," Annu. Rev. Immunol., vol. 18, pp. 767-811 (2000).

Butcher, et al., "Lymphocyte Trafficking and Regional Immunity," Advances in Immunology, vol. 72, pp. 209-253 (1999).

Sprent, et al., "Antigen-Induced Selective Recruitment of Circulating Lymphocytes," Cellular Immunology, vol. 2, pp. 171-181 (1971).

Garside, et al., "Visualization of Specific B and T Lumphocyte Interactions in the Lymph Node," Science, vol. 281, pp. 96-99 (1998).

Jenkins, et al., "In Vivo Activation of Antigen-Specific CD4 T Cells," Annu. Rev. Immunol., vol. 19, pp. 23-45 (2001).

Kaldjian, et al., "Spatial and Molecular Organization of Lymph Node T Cell Cortex: A Labyrinthine Cavity Bounded by an Epithelium-Like Monolayer of Fibroblastic Reticular, Cells Anchored to Basement Membrane-Like Extracellular Matrix," International Immunology, vol. 13, pp. 1243-1253 (2001).

Gretz, et al., "Sophisticated Strategies for Information Encounter in the Lymph Node: The Reticular Network as a Conduit of Soluble Information and a Highway for Cell Traffic," The Journal of Immunology, vol. 157, pp. 495-499 (1996).

Van Den Berg, et al., "Localization of $\beta$ 1 Integrins and Their Extracellular Ligands in Human Lymphoid Tissues," American Journal of Pathology, vol. 143, pp. 1098-1110 (1993).

Gretz, et al., "Lymph-borne Chemokines and Other Low Molecular Weight Molecules Reach High Endothelial Venules Via Specialized Conduits While a Functional Barrier Limits Access to the Lymphocyte Microenvironments in Lymph Node Cortex," The Journal of Experimental Medicine, vol. 192, pp. 1425-1439 (2000).

Stuart, et al., "The Human Reticular Cell: Morphology and Cytochemistry," J. Pathol, vol. 103, pp. 41-47 (1971).

Crivellato, et al., "Stromal Cell Organisation in the Mouse Lymph Node. A Light and Electron Microscopic Investigation Using the Zinc Iodide-Osmium Technique," J. Anat., vol. 190, pp. 85-92 (1997).

Gretz, et al., "Cords, Channels, Corridors and Conduits: Critical Architectural Elements Facilitating Cell Interactions in the Lymph Node Cortex," Immunological Reviews, vol. 156, pp. 11-24 (1997).

Friedl, et al., "CD4+ T Lymphocytes Migrating in Three-Dimensional Collagen Lattices Lack Focal Adhesions and Utilize Beta 1 Integrin-Independent Strategies for Polarization, Interaction with Collagen Fibers and Locomotion," Eur. J. Immunol., vol. 28, pp. 2331-2343 (1998).

Forster, et al., "CCR7 Coordinates the Primary Immune Response by Establishing Functional Microenvironments in Secondary Lymphoid Organs," Cell, vol. 99, pp. 23-33 (1999).

Gunn, et al., "Mice Lacking Expression of Secondary Lymphoid Organ Chemokine Have Defects in Lymphocyte Homing and Dentritic Cell Localization," J. Exp. Med., vol. 189, pp. 451-460 (1999).

Junt, et al., "Antiviral Immune Responses in the Absence of Organized Lymphoid T Cell Zones in *plt/plt* Mice", The Journal of Immunology, vol. 168, pp. 6032-6040 (2002).

Mori, et al., "Mice Lacking Expression of the Chemokines CCL21-ser and CCL19 (plt Mice) Demonstrate Delayed but Enhanced T Cell Immune Responses," J. Exp. Med., vol. 193, No. 2, pp. 207-217 (2001).

Gunzer, et al., "Antigen Presentation in Extracellular Matrix: Interactions of T Cells with Dendritic Cells are Dynamic, Short Lived, and Sequential," Immunity, vol. 13, pp. 323-332 (2000).

Miller, et al., "Two-Photon Imaging of Lymphocyte Motility and Antigen Response in Intact Lymph Node," Science, vol. 296, pp. 1869-1873 (2002).

Stoll, et al., "Dynamic Imaging of T Cell-Dendritic Cell Interactions in Lymph Nodes," Science, vol. 296, pp. 1873-1876 (2002).

Baumgarth, "A Two-Phase Model of B-Cell Activation," Immunological Review, vol. 176, pp. 171-180 (2000).

Fulcher, et al., "B-Cell Activation Versus Tolerance—The Central Role of Immunoglobulin Receptor Engagement and T-Cell Help," Int. Rev. Immunol., vol. 15, pp. 33-52 (1997).

Parker, "T Cell-Dependent B Cell Activation," Annu. Rev. Immunol., vol. 11, pp. 331-360 (1993).

Kosco-Vilbois, "Are Follicular Dendritic Cells Really Good for Nothing," Nature Reviews Immunology, vol. 3, pp. 764-769 (2003).

Skibinski, et al., "Enhancement of Terminal B Lymphocyte Differentiation in Vitro by Fibroblast-Like Stromal Cells from Human Spleen," Eur. J. Immunol., vol. 28, pp. 3940-3948 (1998).

Dubois, et al., "Dendritic Cells Enhance Growth and Differentiation of CD40-Activated B Lymphocytes," J. Exp. Med., vol. 185, pp. 941-951 (1997).

Cyster, et al., "Follicular Stromal Cells and Lymphocyte Homing to Follicles," Immunological Reviews, vol. 176, pp. 181-193 (2000).

Matsumoto, et al., "Affinity Maturation Without Germinal Centres in Lymphotoxin-$\alpha$-Deficient Mice," Nature, vol. 382, pp. 462-466 (1996).

Pasparakis, et al., "Immune and Inflammatory Responses in TNF$\alpha$ Deficient Mice: A Critical Requirement for TNF$\alpha$ in the Formation of Primary B Cell Follicles, Follicular Dendritic Cell Networks and Germinal Centers, and in the Maturation of the Humoral Immune Response," J. Exp. Med., vol. 184, pp. 1397-1411 (1996).

Toyama, et al., "Memory B Cells Without Somatic Hypermutation are Generated from Bcl 6 Deficient B Cells," Immunity, vol. 17, pp. 329-339 (2002).

Galibert, et al., "CD40 and B Cell Antigen Receptor Dual Triggering of Resting B Lymphocytes Turns on a Partial Germinal Center Phenotype," J. Exp. Med., vol. 183, pp. 77-85 (1996).

Razanajaona, et al., "In Vitro Triggering of Somatic Mutation in Human Naïve B Cells," The Journal of Immunology, vol. 159, pp. 3347-3353 (1997).

Phillips, et al., "Activation of Pertussis Toxin-Sensitive CXCL12 (SDF-1) Receptors Mediates Transendothelial Migration of T Lymphocytes Across Lymph Node High Endothelial Cells," Eur. J. Immunol., vol. 32, pp. 837-847 (2002).

Rot, "In Situ Binding Assay for Studying Chemokine Interactions with Endothelial Cells," Journal of Immunological Methods, vol. 273, pp. 63-71 (2003).

Irvine, et al., "Nanoscale Clustering of RGD Peptides at Surfaces Using Comb Polymers. 1. Synthesis and Characterization of Comb Thin Films," Biomacromolecules, vol. 2, pp. 85-94 (2001).

West, et al., "Polymeric Biomaterials with Degradation Sites for Proteases Involved in Cell Migration," Macromolecules, vol. 32, pp. 241-244 (1999).

Bogdan, et al., "Fibroblasts as Host Cells in Latent Leishmaniosis," J. Exp. Med., vol. 191, pp. 2121-2129 (2000).

Castro, et al., "Spleen-Derived Stromal Cells. Adhesion Molecules Expression and Lymphocyte Adhesion to Reticular Cells," Eur. J. Cell. Biol., vol. 74, 321-328 (1997).

Skibinski, et al., "The Role of Hepatocyte Growth Factor and Its Receptor *c-met* in Interactions Between Lymphocytes and Stromal Cells in Secondary Human Lymphoid Organs," Immunology, vol. 102, pp. 506-514 (2001).

LeBedis, et al., "Peripheral Lymph Node Stromal Cells Can Promote Growth and Tumorigenicity of Breast Carcinoma Cells Through the Release of IGF-I and EGF," Int. J. Cancer, vol. 100, pp. 2-8 (2002).

Ruco, et al., "Expression and Cell Distribution of the Intercellular Adhesion Molecule, Vascular Cell Adhesion Molecule, Endothelial Leukocyte Adhesion Molecule, and Endothelial Cell Adhesion Molecule (CD31) in Reactive Human Lymph Nodes and in Hodgkin's Disease," American Journal of Pathology, vol. 140, pp. 1337-1344 (1992).

Cyster, "Chemokines and the Homing of Dendritic Cells to the T Cell Areas of Lymphoid Organs," J. Exp. Med. vol. 189, No. 3, pp. 447-450 (1999).

Ansel, et al., "A Chemokine-Driven Positive Feedback Loop Organizes Lymphoid Follicles," Nature, vol. 406, pp. 309-314 (2000).

Mebius, "Organogenesis of Lymphoid Tissues," Nat. Rev. Immunol, vol. 3, pp. 292-303 (2003).

Poznansky, et al., "Efficient Generation of Human T Cells From a Tissue-Engineered Thymic Organoid," Nature Biotechnology, vol. 18, pp. 729-734 (2000).

Safarik, et al., "Use of Magnetic Techniques for the Isolation of Cells," Journal of Chromatography B, vol. 722, pp. 33-53 (1999).

Dynal (Norway): http://www.invitrogen.com/.

Agowa GMBH (Germany): http://agowade/contentsframes/magneticseparation/particle.html.

Chen, et al., "A Film Tension Theory of Phagocytosis," Journal of Colloid and Interface Science, vol. 190, pp. 118-133 (1997).

Banchereau, et al., "Dendritic Cells and the Control of Immunity," Nature, vol. 392, pp. 245-252 (1998).

Kabashima, et al., "Prostaglandin $E_2$-EP4 Signaling Initiates Skin Immune Responses by Promoting Migration and Maturation of Langerhans Cells," Nature Medicine, vol. 9, pp. 744-749 (2003).

Denkbas, et al., "Magnetic Chotosan Microspheres: Preparation and Characterization," Reactive & Functional Polymers, vol. 50, pp. 225-232 (2002).

Larsson, et al., "Requirement of Mature Dendritic Cells for Efficient Activation of Influenza A-Specific Memory CD8 + T Cells," The Journal of Immunology, vol. 165, pp. 1182-1190 (2000).

Danke, et al., "HLA Class II-Restricted CD4+ T Cell Responses Directed Against Influenza Viral Antigens Postinfluenza Vaccination," The Journal of Immunology, vol. 171, pp. 3163-3169 (2003).

Hasbold, et al., "Quantitative Analysis of Lymphocyte Differentiation and Proliferation in Vitro Using CarboxyFluorescein Diacetate Succinimidyl Ester," Immunology and Cell Biology, vol. 77, pp. 516-522 (1999).

Luk, et al., "Rapid and Sensitive Detection of *Salmonella* (O:6,7) by Immunomagnetic Monoclonal Antibody-Based Assays," Journal of Immunological Methods, vol. 137, pp. 1-8 (1991).

Gundersen, et al., "Magnetic Bead Antigen Capture Enzyme-Linked Immunoassay in Microtitre Trays for Rapid Detection of Schistosomal Circulating Anodic Antigen," Journal of Immunological Methods, vol. 148, pp. 1-8 (1992).

Chou, et al., "The Detection of the HLA-B27 Antigen by Immunomagnetic Separation and Enzyme-Linked Immunosorbent Assay-Comparison with a Flow Cytometric Procedure," Journal of Immunological Methods, vol. 255, pp. 15-22 (2001).

Kourilov, et al., "Magnetic-Bead Enzyme-Linked Immunosorbent Assay Verifies Adsorption of Ligand and Epitope Accessibility," Analytical Biochemistry, vol. 311, pp. 166-170 (2002).

http://www.xcyte.com.

Protocol for anti-CD3 Activation of T-Cells from E-Bioscience (San Diego, CA): http://www.ebioscience..com/ebioscience/appls/AC145.htm.

Kadowaki, et al., "Subsets of Human Dendritic Cell Precursors Express Different Toll-Like Receptors and Respond to Different Microbial Antigens," J. Exp. Med. vol. 194, No. 6, pp. 863-869 (2001).

Sieben, et al., "Comparison of Different Particles and Methods for Magnetic Isolation of Circulating Tumor Cells," Journal of Magnetism and Magnetic Materials, vol. 225, pp. 175-179 (2001).

Regnier, et al., "Integration of Langerhans Cells into a Pigmented Reconstructed Human Epidermis," The Journal of Investigative Dermatology, vol. 109, No. 4, pp. 510-512 (1997).

Abas, et al., "J.S. Cellular and Molecular Immunology," W.B. Sanders Co., New York, NY (2000).

Benbrook et al., "Organotypic cultures represent tumor microenvironment for drug testing," Drug Discovery Today: Disease Models, 3(2), pp. 143-148 (2005).

International Search for PCT/US07/013745, dated Apr. 18, 2008.

H.-J. Kim et al, Establishment of Early Lymphoid Organ Infrastructure in Transplanted Tumors Mediated by Local Production of Lymphotoxin $\alpha$ and in Combined Absence of Functional B and T Cells. In J. of Immunology, vol. 172:4037-4047 (2004).

Portner, R et al, Chapter 2: An Overview on Bioreactor Design, Prototyping, and Process Control for Reproducible Three-Dimensional Tissue Culture. In Drug Testing In Vitro: Breakthrough Cell Cultur Technology. Eds. U. Marx and V. Sandig 2006: Wiley-VCH, pp. 65-69.

Okamoto et al, Artificial Lymph Nodes Induce Potent Secondary Immune Response in Naïve and Immunodeficient Mice. J. Clin. Invest. Apr. 2007, vol. 117, No. 4, pp. 997-1007.

Edelman et al, A Cultureal Renaissance: In Vitro Cell Biology Embraces Three-Dimensional Context. Exp Neurol. 2005, vol. 192, pp. 1-6.

Birkness et al., An In Vitro Tissue Culture Bilayer Model To Examine Early Events in Mycobacterium Tuberculosis Infection, *Infection and Immunity*, Feb. 1999, p. 653-658, vol. 67, No. 2.

Birkness et al., A Tissue Culture Bilayer Model To Study the Passage of Neisseria Meningitidis, *Infection and Immunity*, Feb. 1995, p. 402-409, vol. 63, No. 2.

Weppler et al., Modulation of Endotoxin-Induced Neutrophil Transendothelial Migration by Alveolar Epithelium in a Defined Bilayer Model, *Experimental Lung Research* 32:10, 455-482 (2006).

International Search Report—PCT/US2007/08379.

International Search Report—PCT/US2008/056720.

Sarradell et al. (2003) *Vet. Pathol.*, 40, 395-404.

Oehler et al. (2000) *Ann. Hematol.*, 79, 355-362.

Buehler et al. (2003) *Vaccine*, 21, 877-882.

Dubey et al. (2005) *J. Clin. Endocrin & Met.*, 90, 247-255.

Roos et al. (2005) *Expert Opin. Drug Metab. Toxicol.* 1, 187-202.

Boni et al. (2006) *Eur. J. Immunol.* 36, 3157-3166.

Caux et al. (1995) *J. Immunol.* 155, 5427-5435.

Moser et al. (2000) *Nature Immunol.* 1, 199-205.

Tan et al. (2005) *J. Leuk. Biol.* 78, 319-324.

Aydar et al. (2005) *J. Immunol.* 174, 5358-5366.

Tew et al. (2001) *Trends Immunol.* 22, 361-367.

Wu et al. (2008) *J. Immunol.* 180, 281-290.

Cayeux et al. (1999) *Eur. J. Immunol.* 29, 225-234.

Santini et al. (2000) *J. Exp. Med.* 191, 1777-1788.

International Search Report—PCT/US08/70107.

International Search Report—PCT/US06/048959.

International Search Report—PCT/US07/014826.

International Search Report—PCT/US08/69172, dated Mar. 25, 2009.

International Search Report—PCT/US08/70107, dated Mar. 13, 2009.

D'Amico et al., *Blood* 92:207-214 (1998).

Simmingskoeld et al., *Scand. J. Immunol.* 7:233-238 (1978).

Transwell® Permeable Supports Selection and Use Guide, Corning Corp., pp. 1-12 (2009).

Khademhosseini et al., *"Microscale Technologies for Tissue Engineering and Biology,"* Proc. Natl. Acad. Sci. USA, vol. 103, pp. 2480-2487 (2006).

Dubois et al., J. Leukocyte Biology, 1999, v.66, p. 224-230.

Gansuvd et al., Human Immunol., 2003, v.64, p. 427-439.

Clayton et al., Clin. Exp. Immunol., 2003, v.132, p. 174-179.

\* cited by examiner

DISEASE MODEL INCORPORATION INTO AN ARTIFICIAL IMMUNE SYSTEM (AIS)

CROSS REFERENCE TO RELATED CASES

This application is a continuation-in-part of U.S. application Ser. No. 11/116,234, filed Apr. 28, 2005, and published as US 2005/0282148 on Dec. 22, 2005, which claims the benefit of priority of U.S. Provisional Application Ser. No. 60/565, 846, filed Apr. 28, 2004 and 60/643,175, filed Jan. 13, 2005. This application also claims the benefit of priority of International Application No. PCT/US2005/014444, filed Apr. 28, 2005. Each of these applications is hereby incorporated by reference in their entirety.

BACKGROUND OF THE INVENTION

1. Field of the Invention

The present invention is directed to a method for developing a disease model that may be integrated with an artificial human immune system for in vitro testing of vaccines, adjuvants, immunotherapy candidates, cosmetics, drugs, biologics, and other chemicals. The disease model and artificial immune system of the present invention is useful for assessing the anti-microbial and/or anti-cancer capacity of vaccines, drugs, biologics, immunotherapeutics, and adjuvants in the context of an in vitro challenge with disease agents. Embodiments of the present invention can be used to accelerate and improve the accuracy and predictability of vaccine and drug development.

2. Background of the Technology

Despite the advent and promise of recent technologies, including combinatorial chemistry, high-throughput screening, genomics, and proteomics, the number of new drugs and vaccines reaching the market has not increased. In fact, the attrition rate within drug discovery programs exceeds 90%.

The introduction of these new (and expensive) technologies has not reduced the lost opportunity costs associated with immunotherapy development; rather, these costs have increased. Indeed, it is now estimated that almost $1 billion is required to bring a new drug to the market.

The development and biological testing of human vaccines has traditionally relied on small animal models (e.g., mouse and rabbit models) and then non-human primate models. However, such small animal models are expensive and non-human primate models are both expensive and precious. Furthermore, there are many issues regarding the value of such animal studies in predicting outcomes in human studies.

A major problem remains the translation from test systems to human immunology. Successful transfer between traditional testing systems and human biology requires an intricate understanding of disease pathogenesis and immunological responses at all levels. Given worldwide health problems caused by known and emerging infectious agents and even potential biological warfare pathogens, it is time for a fresh approach to understanding disease pathogenesis, the development and rapid testing of vaccines, and insights gathered from such work.

The body's distributed immune system can be roughly divided into four distinct compartments: tissues and blood, mucosal tissues, body cavities, and skin. Because of ease of study, most is known about the tissue and blood compartment and its lymphoid tissues, the spleen and lymph nodes.

The mammalian immune system uses two general mechanisms to protect the body against environmental pathogens. The immune system recognizes and responds to structural differences between self and non-self proteins. Proteins that the immune system recognizes as non-self are referred to as antigens. Pathogens typically express large numbers of complex antigens. When a pathogen-derived molecule is encountered, the immune response becomes activated to enable protection against that pathogenic organism.

The first immune system mechanism is the non-specific (or innate) inflammatory response. The innate immune system appears to recognize specific molecules that are present on pathogens but not on the body itself.

The second immune system mechanism is the specific or acquired (or adaptive) immune response. Acquired immunity is mediated by specialized immune cells called B and T lymphocytes (or simply B and T cells). Acquired immunity has specific memory for antigenic structures; repeated exposure to the same antigen increases the response, which increases the level of induced protection against that particular pathogen. Whereas innate responses are fundamentally the same for each injury or infection, acquired responses are custom-tailored to the pathogen in question. The acquired immune system evolves a specific immunoglobulin (antibody) response to many different molecules present in the pathogen, called antigens. In addition, a large repertoire of T cell receptors (TCR) is sampled for their ability to bind processed forms of the antigens bound to major histocompatibility complex (MHC, also known as human leukocyte antigen, HLA) class I and II proteins on the surface of antigen-presenting cells (APCs), such as dendritic cells (DCs).

B cells produce and mediate their functions through the actions of antibodies. B cell-dependent immune responses are referred to as "humoral immunity," because antibodies are found in body fluids.

T cell-dependent immune responses are referred to as "cell-mediated immunity," because effector activities are mediated directly by the local actions of effector T cells. The local actions of effector T cells are amplified through synergistic interactions between T cells and secondary effector cells, such as activated macrophages. The result is that the pathogen is killed and prevented from causing diseases.

The functional element of a mammalian lymph node is the follicle, which develops a germinal center (GC) when stimulated by an antigen. The GC is an active area within a lymph node, where important interactions occur in the development of an effective humoral immune response. Upon antigen stimulation, follicles are replicated and an active human lymph node may have dozens of active follicles, with functioning GCs. Interactions between B cells, T cells, and FDCs take place in GCs.

Various studies of GCs in vivo indicate that the many important events occur there, including immunoglobulin (Ig) class switching, rapid B cell proliferation (GC dark zone), production of B memory cells, accumulation of select populations of antigen-specific T cells and B cells, hypermutation, selection of somatically mutated B cells with high affinity receptors, apoptosis of low affinity B cells, affinity maturation, induction of secondary antibody responses, and regulation of serum immunoglobulin G (IgG) with high affinity antibodies. Similarly, data from in vitro GC models indicate that FDCs are involved in stimulating B cell proliferation with mitogens and it can also be demonstrated with antigen (Ag), promoting production of antibodies including recall antibody responses, producing chemokines that attract B cells and certain populations of T cells, and blocking apoptosis of B cells.

Similar to pathogens, vaccines function by initiating an innate immune response at the vaccination site and activating antigen-specific T and B cells that can give rise to long term memory cells in secondary lymphoid tissues. The precise interactions of the vaccine with cells at the vaccination site and with T and B cells of the lymphoid tissues are important to the ultimate success of the vaccine.

Almost all vaccines to infectious organisms were and continue to be developed through the classical approach of generating an attenuated or inactivated pathogen as the vaccine itself. This approach, however, fails to take advantage of the recent explosion in our mechanistic understanding of immunity. Rather, it remains an empirical approach that consists of making variants of the pathogen and testing them for efficacy in non-human animal models.

Advances in the design, creation and testing of more sophisticated vaccines have been stalled for several reasons. First, only a small number of vaccines can be tested in humans, because, understandably, there is little societal tolerance for harmful side effects in healthy people, especially children, exposed to experimental vaccines. With the exception of cancer vaccine trials, this greatly limits the innovation that can be allowed in the real world of human clinical trials. Second, it remains challenging to predict which epitopes are optimal for induction of immunodominant CD4 and CD8 T cell responses and neutralizing B cell responses. Third, small animal testing, followed by primate trials, has been the mainstay of vaccine development; such approaches are limited by intrinsic differences between human and non-human species, and ethical and cost considerations that restrict the use of non-human primates. Consequently, there has been a slow translation of basic knowledge to the clinic, but equally important, a slow advance in the understanding of human immunity in vivo.

The artificial immune system (AIS) of the present invention can be used to address this inability to test many novel vaccines in human trials by instead using human tissues and cells in vitro. The AIS enables rapid vaccine assessment in an in vitro model of human immunity. The AIS provides an additional model for testing vaccines in addition to the currently used animal models.

Attempts have been made in modulating the immune system. See, for example, U.S. Pat. No. 6,835,550 B1, U.S. Pat. No. 5,008,116, Suematsu et al., [Nat Biotechnol, 22, 1539-1545, (2004)] and U.S. Patent Application No. 2003/0109042.

Nevertheless, none of these publications describe or suggest an artificial (ex vivo) human cell-based, immune-responsive system comprising a vaccination site (VS), a lymphoid tissue equivalent (LTE), and disease models. The present invention comprises such a system and its use in assessing the interaction of substances with the immune system.

A primary goal of a preclinical testing program is to improve outcome for patients by the early identification of potential applications for new vaccine or drug agents before clinical development. The premise for establishing an in vitro testing effort is that it will allow vaccine candidates to be selected for clinical evaluation with increased likelihood for clinical benefit. Clearly, this requires that the in vitro system be predictive of human responses to the vaccine and the efficacy of the vaccine against the disease in question. In the absence of an effective and predictive preclinical testing program, ineffective vaccines are likely to be selected for evaluation, thus slowing progress in improving outcomes. Furthermore, having an in vitro testing system that is predictive (a "clinical trial in a test tube") will significantly reduce lost opportunity costs associated with vaccine testing. That is, if a vaccine candidate is going to fail, it should fail early.

The development of an artificial immune system coupled with a disease model has the potential to change the way vaccine formulations are tested. The preclinical in vitro testing program of the present invention, though based on both immunologic and engineering principles, has the very pragmatic objective of providing reliable, predictive, and reproducible information to clinical investigators to allow enlightened prioritization among the multiple vaccine/adjuvant formulations available. Clearly, that is a goal of all preclinical testing, but what is new in the in vitro testing system of the present invention is an in vitro model using functionally equivalent tissue engineered constructs populated with human cells. In comparison with in vivo animal testing, in vitro testing using the system comprising the present invention is less expensive, less time-consuming, and importantly more predictive of clinical outcomes.

Although historically mice have been used for studying tumor genetics, physiology, and therapeutic regimens, murine tissue models have many limitations. An important difference is that human tumors are primarily epithelial in origin, whereas murine tumors are typically non-epithelial (such as sarcomas, lymphomas). Many agents that are carcinogenic in mice are not in humans, and vice versa. Oncogenic pathways are different in many ways in the mouse compared to humans. Additionally, the murine basal metabolic rate is six times higher than in humans. New approaches have examined xenograft placement on immune-deficient mice with more success; however, the murine component still exists in this model. (Ortiz-Urda et al. (2002) Nature Med 8, 1166-70). Thus, studying human tumor models in a human cell-based VS of the present invention removes these interspecies differences.

Embodiments of the present invention combine the predictive power of a functional immune model integrated with a tissue engineered disease model. Coupled with the technological advantages of high-throughput fabrication and testing, the present invention facilitates the identification of disease-related vaccines.

For tumor or viral disease models, simple monolayer and suspension cultures are commonly used. However, they provide a highly artificial cellular environment for target screening and vaccine development. Vaccine/adjuvant screening requires in vitro disease models that mimic the human disease (e.g., cancer) with increased accuracy to usefully aid in the selection of potential effectors.

Recent work by Mertsching and colleagues at the Fraunhofer Institute of Interfacial Engineering and Biotechnology, Germany, is beginning to demonstrate that in vitro 3D models can be a useful platform in cancer research. They developed a new, 3D, vascularized tissue construct. The vascularized 3D matrix is populated with endothelial cells and then with tumor cells to create an ex vivo vascularized tumor-like structure as a disease model. Their data suggests that this in vitro model offers the possibility to simulate physiological drug application and provide a human 3D test system for cancer research/therapy.

SUMMARY OF THE INVENTION

The present invention is directed to an artificial immune system to permit the assessment of agents without administration to animal subjects.

The present invention is also directed to a method of using the artificial immune system of the invention for evaluating the potential reaction of a diseased animal to an agent.

DETAILED DESCRIPTION OF THE INVENTION

Figure 1A:
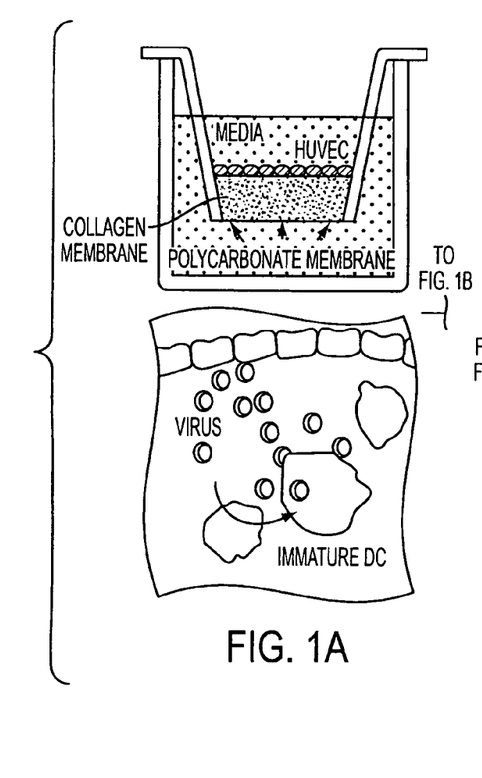
FIG. 1. Depicts a schematic illustration of an embodiment of the invention, showing the integration of the AIS and a disease model.
Figure 1B:
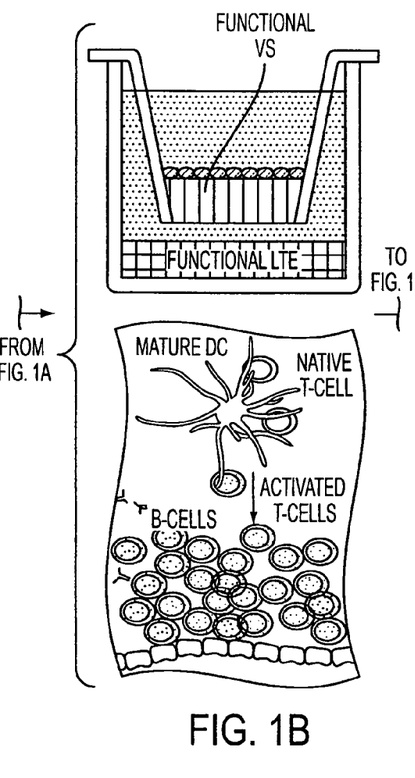
Figure 1C:
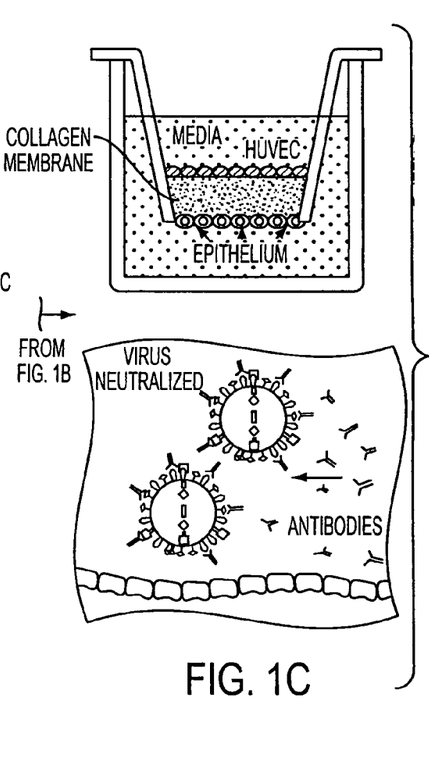
Figure 2A:
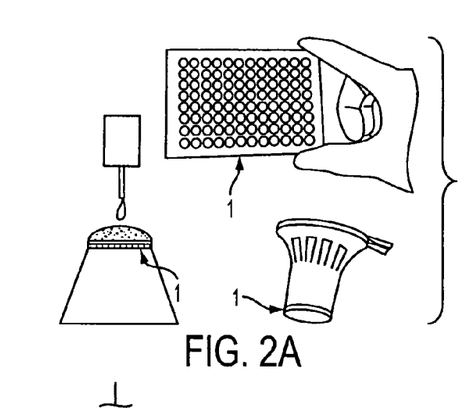
FIG. 2. Shows a 3D heterogeneous tissue construct, comprising the addition of cells on the top and bottom of the construct, to create endothelial and epithelial layers.
Figure 2B:
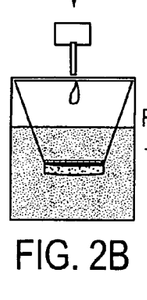
Figure 2C:
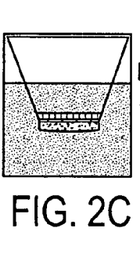
Figure 2D:
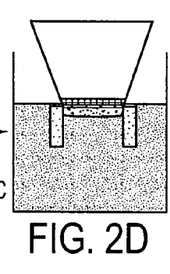
Figure 2E:
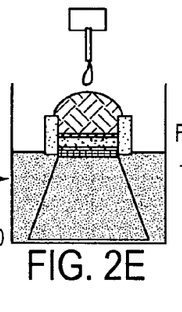
Figure 2F:
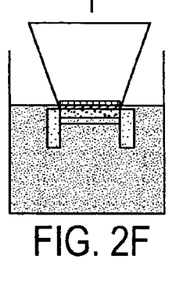
Figure 2G:
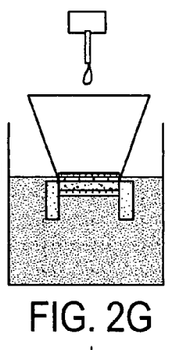
Figure 2H:
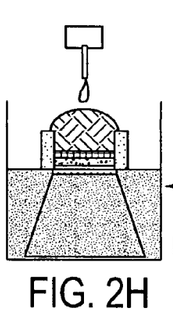
Figure 2I:
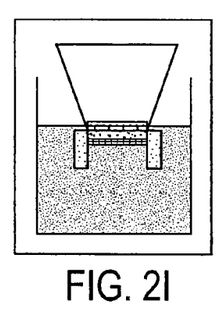

The present invention comprises the use of an artificial immune system (AIS) with disease models to provide essentially the ability to conduct a "clinical trial in a test tube," That is the ability to determine the efficacy of neutralizing antibodies, cytolytic T cells, and associated biomolecules on the disease model, which can be, for example, tumoral, viral, or bacterial in nature. FIG. 1 illustrates schematically an example of the integration of the AIS and a disease model. As an example, schematically, the VS is where infection occurs, the LTE is where immune induction occurs, and the disease model is where the immune response to the disease occurs.

The present invention comprises the use of disease models to test the efficacy of vaccine formulations. In embodiments of the present invention we use cell lines in 2D culture and cell lines placed with a 3D tissue-engineered construct. As examples, disease models of the present invention include viral (e.g., herpes simplex virus, hepatitis A, B, C, VSV, HIV, vaccinia virus, influenza virus), tumoral (e.g., melanoma) and autoimmune models (e.g., RA, diabetes, psoriasis, Crohn's) The infected or diseased cells are included in the engineered tissue construct. For example, virally infected epithelial cells can be used in a tissue engineered skin or mucosal equivalent. As another example, herpes simplex viruses are ectodermotropic (i.e., they can infect and reproduce in epithelial cells and reside in neurons in a latent state).

EXAMPLES

Example 1

Generic Tissue Construct for a 3D In Vitro Disease Model

FIG. 2 illustrates a 3D heterogeneous tissue construct, comprising the addition of cells on the top and bottom of the construct, to create endothelial and epithelial layers. This model is an improvement on our established 3D endothelial cell-only construct, which has been used for transendothelial migration and for monocyte to dendritic cell and macrophage differentiation (the vaccination site, VS).

The 3D model of this example can be used to study immunophysiological reactions when subjected to various diseases and vaccine formulations. This is a generic construct because most tissues involve a 3D extracellular matrix with associated endothelial and epithelial layers The disease, whether viral, bacterial, or tumoral, is introduced into the generic tissue construct. The various immunocytes and biomolecules from the AIS (e.g., antibodies, T cells, cytokines, chemokines) can then be delivered to the disease model to examine and detect effector responses (e.g., the presence or absence of neutralizing antibodies, cytotoxicity).

Example 2

Tumor Modeling in the AIS using Melanoma Cells.

Many in vitro model systems have been used for examining the effects of anti-cancer therapeutics and tumor growth in adult and childhood cancers, using both primary cells and various cell lines (see, e.g., Houghton et al. (2002) *Clin Cancer Res* 8, 3646-57). Such models have proven useful for assessing tumor metabolic states, inhibition of proliferation, and decreases in overall biomass (see, e.g., Monks et al., (1991) *J Natl Cancer Inst* 83, 757-66; Scherf et al., (2000) *Nat Genet* 24, 236-44).

Animal models of human cancers have not been good predictors of human therapeutic outcome because of species differences (see, e.g., Houghton et al., (2002) *Clin Cancer Res* 8, 3646-57; Bridgeman et al., (2002) *Cancer Res* 60, 6573-6; Batova et al., (1999), *Cancer Res* 59, 1492-7).

As with any tumor model, the primary end goal is to increase patient survival and overall well being and to decrease tumor burden. The most predictive model will aid in correlating between what is observed in vitro with what is observed in the clinical setting. Melanocytes in human skin are inter-follicular melanin-containing (pigmented) cells within the epithelial stratum and are of neuroectodermal origin. Melanoma is a common form of human skin cancer. Malignant melanoma (both pigmented and non-pigmented forms) are frequently resistant to interventional therapies and are associated with significant morbidity and mortality.

Two modes of melanoma cellular proliferation are known to occur: one in a radial direction and the other in a vertical direction, into the subepithelial matrix (dermal layer in vivo) (Chudnovsky et al., (2005) *Nat Genet* 37, 745-9). Many factors have been implicated in spontaneous, uncontrolled proliferation including genetic alterations, overexpression of the catalytic subunit of human telomerase reverse transcriptase (TERT) and expression of melanoma markers HMB-45 and Melan-A. Pagetoid invasion into upper epithelial and dermis layers is typically observed under these conditions. Various melanoma cells can be purchased from ATCC (e.g., A-375, SK-Mel-31, WM115, SK-Mel-2, SK-Mel-24) with varying characteristics as to invasion properties (vertical or radial) and expression of specific human melanoma markers (e.g., NRAS, PI3K, CDK4, HMB-45 or Melan-A).

Example 3

Heterogeneous Tissue Constructs with the Addition of Cells on the Top and Bottom of the Tissue Construct to Form Endothelial and Epithelial Layers.

Figure 3:
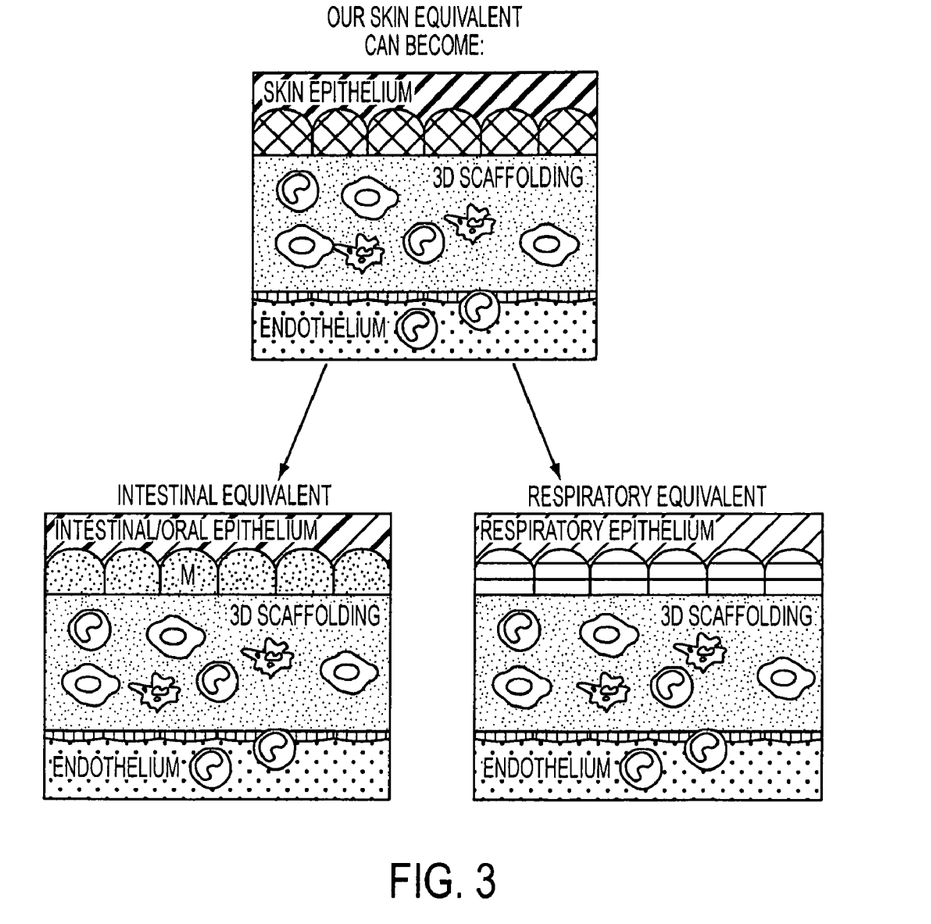
FIG. 3. Is a schematic representation of the development of the generic disease model and how it can be tested with a particular disease.
Figure 4A:
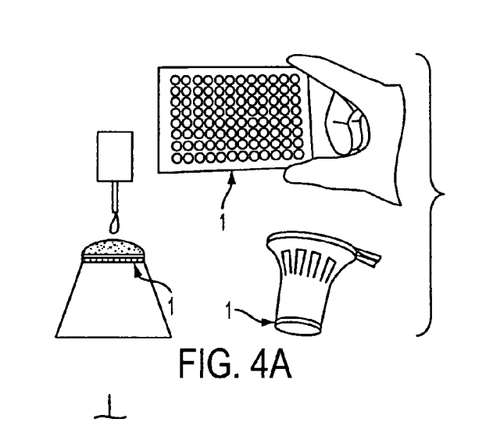
FIG. 4. Is a schematic illustration of, as an example, vertically expanding melanoma tumor cells or bacterially or virally infected fibroblast cells inside the 3D construct.
Figure 4B:
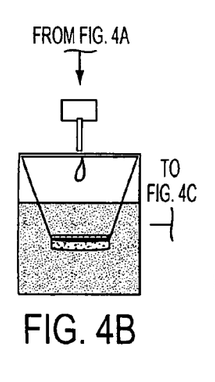
Figure 4C:
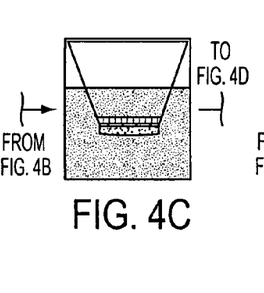
Figure 4D:
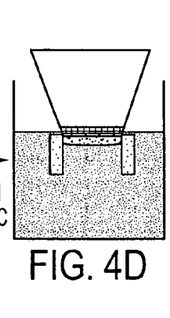
Figure 4E:
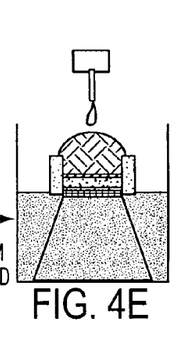
Figure 4F:
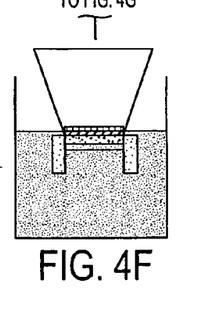
Figure 4G:
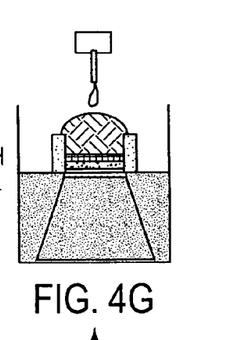
Figure 4H:
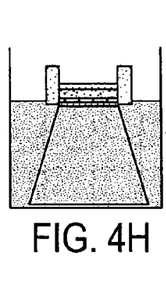
Figure 4I:
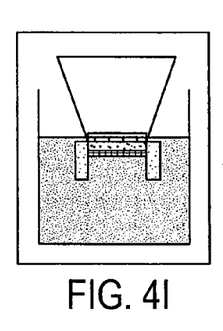

A schematic representation of the development of the generic disease model and how it can be tested with a particular disease is shown in FIG. 3. As an example, we used a polycarbonate membrane support structure to prepare a 3D ECM matrix, comprising either collagen, synthetic or natural materials (e.g., hydrogels, PLA, PLGA, gelatin, hyaluronic acid), or combinations thereof. We have established an ECM that is capable of supporting two cell layers. We first grow a layer of epithelial cells (e.g., human keratinocytes) on one side of the matrix. An advantage of this model is that other epithelial cells can be used, such as respiratory epithelial cells, skin epithelial cells, or intestinal/oral epithelial cells (as schematically illustrated in FIG. 3). The basement membrane zone between the epithelium and the matrix is important to the success of this aspect of the construct and additions, such as collagen types IV or VII can be included. For a melanoma model the barrier function of the basement membrane may also be important in dissecting the pathology of modes of metastasis. This is an advantage of the general architecture of the disease model of the present invention; it can be used to mimic many tissues by using different epithelial cell types. After melanocyte and keratinocyte seeding and when the keratinocytes have become established and begun stratification, the cells are exposed to an air interface, to encourage continued stratification, formation of tight cell junctions, and keratinization.

When a keratinized cell layer is formed, the construct can be inverted, so that a layer of endothelial cells (e.g., HUVECs, immortalized endothelial cell lines) can be applied to the other side. When the endothelial cells have established, the construct can be inverted (so it will be upright again) to reinstate the air interface for the keratinocytes. When the endothelial cells form a confluent monolayer, the tissue construct is complete and ready for characterization.

In other embodiments of the present invention, in a multifunctional disease model without melanocytes in epithelial layer, a viral or bacterial disease model can be prepared. In these embodiments, either the viral or bacterial component is applied to the specialized, non-keratinized epithelial surface, mimicking normal physiologic events. In viral and bacterial invasion/infection, epithelial compromise is caused by either cellular infection or release of bacterial toxins, which can also be monitored.

Example 4

Viability of the 3D Generic Disease Tissue Constructs.

Studies of keratinocytes have shown the cells to remain viable in culture for several weeks (Boelsma et al., (2000) *Acta Derm Venereol* 80, 82-8). We also have experience of maintaining HUVECs in culture and on a 3D construct for several weeks. Viability of the cells on the construct can be monitored by, for example, such methods as identifying any morphological changes and by the classic LDH release assay. As cells die, the plasma membrane becomes leaky with LDH being released into the culture medium and can be measured with a coupled enzymatic assay that results in the conversion of resazurin into a fluorescent resorufin product. The amount of fluorescence produced is proportional to the number of lysed cells. Cell staining can also be performed on the tissue constructs to measure live/dead cell populations. Cell-permeant esterase substrates, such as CellTracker Green CMFDA, serve as viability probes that measure both cell membrane integrity, required for intracellular retention of the probe, and enzymatic activity, required to activate the fluorescence of the probe. Cell-impermeant nucleic acid stains, such as ethidium homodimer-1, can be used to detect dead cells. Fluorescently stained cells can then be observed by confocal microscopy.

Example 5

Epithelial Cells Form Stratified Layers on the Constructs.

For the construction of the skin equivalent model, the keratinocyte layer is exposed to an air interface to encourage formation of stratified layers. The formation of the stratified layers can be monitored by microscopic examination. Periodically cell layers can be examined by using immunofluorescence confocal microscopy to identify the tight junctions and nuclei of the cells. Additionally, samples can be fixed in paraformaldehyde, embedded in parafin, cut into sections, and stained with haematoxylin and eosin for light microscopic examination.

Example 6

Construction of a Generic Tissue Module Creating an In Vitro Disease Model.

In embodiments of the present invention, the 3D model is examined to observe immune- or inflammation-mediated responses to various diseases (e.g., tumors, models). As examples, melanoma cells, HSV, and influenza virus are used.

Melanoma cells are incorporated when the epithelial layer is formed. As human melanocytes are interfollicular, basal epithelial cells, using a cell line that is slower growing allows keratinized epithelial formation. Application of different cell types can be accomplished by intermixing these cells with normal keratinocytes (for example, at a ratio of ~5×10$^3$ to ~30×10$^3$). Monitoring of the vertical and lateral spread of the malignant melanocytes can be accomplished by staining with fluorochrome-labeled, melanocyte-specific markers and confocal microscopy. As another example, other constructs can be digested and the number of melanocytes present can be assessed using flow cytometry and similar markers.

Example 7

As an example, a methodology that can be used to add vertically expanding melanoma tumor cells or bacterially or virally infected fibroblast cells inside the 3D construct, is illustrated schematically in FIG. 4. To add tumor cells to the disease model, we mix these cells within the ECM material before it is added to the membrane support and before we begin to grow the epithelial and endothelial cells on the matrix.

Example 8

For the preparation of a viral model, there are several relevant methods. As an example, for live a virus, we would infect an epithelial layer. As another example, virus-infected irradiated fibroblasts can be incorporated in the collagen matrix. HLA-matched, syngeneic or autologous fibroblasts can be used; they can be propagated and infected with virus at an appropriate multiplicity of infection (MOI) (e.g., ~10). Infection is allowed to proceed until an appropriate time post-infection, at which time infectious virus is UV-inactivated.

Example 9

In vitro infection/disease models are important for an analysis of the viral life cycle, including attachment, entry, and uncoating, and to unravel the interactions between viral particles and host target cells. We can also use the in vitro disease/infection model to examine the efficacy of the vaccine-induced immune products created in the AIS. Suitable example viral disease models include Herpes simplex viruses (HSV) and influenza viruses. Human and/or murine model systems can be used.

Example 10

The present invention comprises both two- and three-dimensional (2D, 3D) models of infection/immune induction. In an example 2D model, a static culture system can be employed. In an example 3D model, the vaccination site (VS) and lymphoid tissue equivalent (LTE) can be used.

Example 11

Several methods of viral antigen introduction are suitable for practicing the present invention. As an example, direct infection of cultured epithelium (?) with virus at an appropriate multiplicity of infection (MOI) can be used. As another, example, HLA-matched or syngeneic fibroblasts can be used; they can be propagated and infected with virus at an appropriate MOI (e.g., ~10). Infection will be allowed to proceed until an appropriate time post-infection at which time infectious virus will be UV-inactivated. The kinetics of virus infection and inactivation can be confirmed by, for example, immunofluorescence and plaque assay, respectively.

Infectious virus or virus-infected UV-inactivated fibroblasts can be added to the cultures. For fibroblast cultures, uninfected UV-treated fibroblasts can be used as negative controls.

In 2D cultures, infectious virus, fibroblasts or vaccine/adjuvant formulations are added to a mixed immunocyte population containing antigen presenting cells (APCs) and lymphocytes.

For 3D culture, antigens are introduced into a vaccination site (VS) containing reverse-transmigrated (RT) antigen presenting cells (APCs), comprising dendritic cells (DCs). APCs then process the antigen and are introduced into the lymphoid tissue equivalent (LTE), comprising T and B lymphocytes.

In both 2D and 3D cultures, immunological parameters of interest include patterns of immunocyte phenotype and cytokine synthesis and secretion. Flow cytometric analysis is valuable in this regard. Virus-specific cytotoxic activity can be assessed for T cells using, for example, a non-radioactive LDH cytoxicity assay with virus-pulsed target cells. B cells can be evaluated for specificity and isotype of antibody secretion, as well as neutralizing capability.

To evaluate recall responses and anti-viral activity, immunocytes and/or soluble factors can be recovered from 2D cultures or from the LTE of the 3D system for analysis. These immunocytes and/or biomolecules can then be tested, for example, using an in vitro 2D, an in vitro 3D tissue engineered disease model, or an in vivo (especially murine) disease model. In 2D experiment, these can be co-cultured with, for example, suspension or monolayer cultures of fibroblasts. The cultures can then be challenged with infectious virus or virus-infected UV-inactivated cells. As another example, a similar in vitro challenge can be performed in the 3D tissue engineered disease model incorporating an epithelial layer.

In the in vitro experiments, cultures are harvested at selected times post-challenge and assayed for virus-specific immunity and anti-viral activities, as indicated, for example, by titers of infectious virus recovered.

To assess the in vivo efficacy of immunocytes derived from the LTE, we can conduct adoptive transfer studies in, for example, a mouse model where selected cell populations derived from the AIS can be introduced prior to viral challenge. Several murine models of HSV infection are available and can be used to assess protective efficacy of cells recovered from the AIS.

Example 12

As another example of the present invention, we can conduct an 'experiment of nature' involving seropositive individuals with recurrent HSV (S$^+$R$^+$), seropositive individuals without recurrent disease (S$^+$R$^-$) and seronegative (S$^-$R$^-$) human subjects. Cells from these subjects can be sensitized with viral antigens. Subsequent immunological read-outs can allow for discrimination of primary and recall immune events and immune profiling of protective immune mechanisms when comparing S$^+$R$^+$ and S$^+$R$^-$ subjects.

Example 13

In a melanoma tumor model, the spread of the melanocytes radially through the epithelial layer and penetration into the sub-epithelial matrix (vertical tumor expansion) can be examined. As some melanoma cell lines exhibit radial expansion only (possibly the result of the impediment of the basement membrane structure or biochemical makeup of the different collagens) or vertical expansion only, it is possible to target the immunocyte population within the matrix. The presence of melanoma antigen with or without the addition of adjuvants, will lead to the maturation of DCs that have captured antigen.

As the APCs reverse transmigrate out of the module with captured antigens, they can be matured with TNFα. APC phenotypic markers and a panel of inflammatory cytokines can be compared to modules without melanoma cell additions. These results can then be compared to VS responses with known stimulants or adjuvants (such as LPS, CpG, poly (IC), MF59). Functional assessment of these monocyte-derived APCs after exposure to tumor antigens from the melanoma cells in the VS, can be conducted by placement into the LTE module for assessment of antigen presentation. IL12 is an important cytokine released by DCs activating T helper cells, which then release IFNγ. IFNγ contributes to CTL activity and B cell differentiation into plasma cells. Antibody release, compliment fixation, and influx of PMNs to the region of the tumor cells (in vivo) causes release of TNFα. TNFα and IFNγ have tumor cytostatic properties. (Croci et al. (2004) *Cancer Res* 64, 8428-34) and can be monitored. As an example, a non-radioactive cytotoxicity T cell assay monitoring LDH release can be used.

What is claimed is:

1. An in vitro three culture cellular system, comprising:
   (i) a vaccination site (VS) culture comprising a first substantially planar matrix, a plurality of cells consisting of endothelial cells and/or epithelial cells attached to said first matrix and a test agent, for receiving a population of peripheral blood mononuclear cells (PBMCs) and for maturing dendritic cell precursors present in said population of PBMCs;
   (ii) a three-dimensional artificial lymphoid tissue equivalent (LTE) culture comprising a second matrix and a plurality of lymphocytes attached to said second matrix, for receiving dendritic cells matured in said VS culture; and
   (iii) a diseased cell culture for receiving immunocytes and/or soluble factors from the LTE culture.

2. The in vitro cellular system of claim 1, wherein said diseased cell culture comprises a two-dimensional cell culture.

3. The in vitro cellular system of claim 1, wherein said diseased cell culture comprises a three-dimensional engineered tissue construct.

4. The in vitro cellular system of claim 3, wherein said three-dimensional engineered tissue construct is a tissue-engineered skin equivalent.

5. The in vitro cellular system of claim 3, wherein said three-dimensional engineered tissue construct is a tissue-engineered mucosal equivalent.

6. The in vitro cellular system of claim 1, wherein said diseased cell culture comprises cells selected from the group consisting of virally infected cells, bacterially infected cells, tumor cells, and autoimmune disease-afflicted cells.

7. The in vitro cellular system of claim 1, wherein said test agent is selected from the group consisting of vaccines, adjuvants, immunotherapy candidates, cosmetics, drugs, biologics, and chemical compounds.

8. The in vitro three culture cellular system of claim 1, wherein said VS culture comprises a plurality endothelial cells attached to one side of the planar matrix and a plurality of epithelial cells attached to the opposing side of the planar matrix.

9. The in vitro three culture cellular system of claim 8, wherein the plurality of epithelial cells is selected from the group consisting of keratinocytes, respiratory epithelial cells, skin epithelial cells, intestinal epithelial cells and oral epithelial cells.

10. The in vitro three culture cellular system of claim 8, wherein the plurality of endothelial cells is human umbilical vein epithelial cells.

11. The in vitro three culture cellular system of claim 1, wherein the plurality of epithelial cells further comprises melanoma cells.

* * * * *

UNITED STATES PATENT AND TRADEMARK OFFICE
CERTIFICATE OF CORRECTION

PATENT NO. : 7,709,256 B2
APPLICATION NO. : 11/453003
DATED : May 4, 2010
INVENTOR(S) : William L. Warren et al.

Page 1 of 1

It is certified that error appears in the above-identified patent and that said Letters Patent is hereby corrected as shown below:

Column 1, at line 3 insert:

--STATEMENT REGARDING FEDERALLY SPONSORED RESEARCH

This invention was made with government support under contract number NBCHC060058, awarded by the Defense Advanced Research Projects Agency, issued by the U.S. Army Medical Research Acquisition Activity, and administered by the U.S. Department of the Interior-National Business Center. The government has certain rights in the invention.--

Signed and Sealed this

Seventeenth Day of August, 2010

David J. Kappos
*Director of the United States Patent and Trademark Office*